United States Patent
Tesar

(10) Patent No.: US 10,502,284 B2
(45) Date of Patent: Dec. 10, 2019

(54) SPRING AUGMENTED ORTHOTIC OR PROSTHETIC EQUIPPED WITH A COMPACT PARALLEL ECCENTRIC ACTUATOR

(71) Applicant: Delbert Tesar, Austin, TX (US)

(72) Inventor: Delbert Tesar, Austin, TX (US)

(73) Assignee: Delbert Tesar, Austin, TX (US)

( * ) Notice: Subject to any disclaimer, the term of this patent is extended or adjusted under 35 U.S.C. 154(b) by 120 days.

(21) Appl. No.: 15/007,152

(22) Filed: Jan. 26, 2016

(65) Prior Publication Data

US 2016/0138679 A1 May 19, 2016

Related U.S. Application Data

(63) Continuation-in-part of application No. 14/869,994, filed on Sep. 29, 2015, now Pat. No. 9,915,319.
(Continued)

(51) Int. Cl.
*F16H 1/32* (2006.01)
*A61H 3/00* (2006.01)
(Continued)

(52) U.S. Cl.
CPC ............... *F16H 1/32* (2013.01); *A61F 2/68* (2013.01); *A61H 3/00* (2013.01);
(Continued)

(58) Field of Classification Search
None
See application file for complete search history.

(56) References Cited

U.S. PATENT DOCUMENTS 2,748,610 A * 6/1956 De Wolf Schatzel .... F16H 1/32
475/162
5,468,193 A * 11/1995 Yamaguchi ............... F16H 1/32
419/37
(Continued)

FOREIGN PATENT DOCUMENTS

WO 2006/125282 A1 11/2006

OTHER PUBLICATIONS

Bram Vanderborght, Nikos G. Tsagarakis, Claudio Semini, Ronald Van Ham, Darwin G. Caldwell, "MACCEPA 2.0: Adjustable Compliant Actuator with Stiffening Characteristic for Energy Efficient Hopping", 2009 IEEE International Conference on Robotics and Automation (Kobe International Conference Center, Kobe, Japan, May 12-17, 2009).
(Continued)

*Primary Examiner* — Justin Holmes
(74) *Attorney, Agent, or Firm* — John A. Fortkort; Fortkort & Houston PC

(57) ABSTRACT

An orthotic or prosthetic actuator is provided which includes a parallel eccentric gear train which terminates on a first end in a first plate, and which terminates on a second end in a second, rotatable plate which is adjacent to the first plate. The actuator further includes a spring which is disposed between these adjacent plates. The actuator preferably utilizes Oldham coupling, by way of a pair of crosslinks disposed on each side of the motor, to restrain rotation of the dual parallel eccentric gears in the actuator, while permitting their linear oscillation. The crosslinks are preferably equipped with a tongue/spline lubrication system to provide continuous lubrication to the mated and loaded crosslink tongue and groove surfaces.

16 Claims, 5 Drawing Sheets

Related U.S. Application Data

(60) Provisional application No. 62/107,734, filed on Jan. 26, 2015, provisional application No. 62/057,216, filed on Sep. 29, 2014, provisional application No. 62/210,223, filed on Aug. 26, 2015.

(51) Int. Cl.
*A61F 2/68* (2006.01)
*A61F 2/50* (2006.01)
*F16H 57/04* (2010.01)

(52) U.S. Cl.
CPC ............... *A61F 2002/5072* (2013.01); *A61F 2002/6836* (2013.01); *F16H 57/0436* (2013.01); *F16H 57/0486* (2013.01)

(56) References Cited

U.S. PATENT DOCUMENTS

| | | | | |
|---|---|---|---|---|
| 5,683,323 | A * | 11/1997 | Imase | F16H 1/32 475/168 |
| 2002/0012595 | A1* | 1/2002 | Kouno | F04B 39/1013 417/559 |
| 2002/0104267 | A1* | 8/2002 | Sato | E05F 11/445 49/350 |
| 2006/0199692 | A1* | 9/2006 | Janek | F16H 1/32 475/162 |
| 2007/0270976 | A1* | 11/2007 | DeHarde | A61F 5/0125 623/27 |
| 2008/0108918 | A1* | 5/2008 | Joutras | A61H 1/02 601/34 |
| 2010/0048342 | A1* | 2/2010 | Chadwick | F16H 1/32 475/181 |
| 2013/0009522 | A1* | 1/2013 | Ozaki | H02K 7/116 310/67 R |
| 2015/0176583 | A1* | 6/2015 | Murase | F04C 23/02 418/54 |
| 2015/0351938 | A1 | 12/2015 | Moser et al. | |
| 2015/0374573 | A1 | 12/2015 | Horst | |
| 2016/0030202 | A1 | 2/2016 | Nishikawa | |
| 2016/0030272 | A1 | 2/2016 | Angold | |
| 2016/0067058 | A1 | 3/2016 | Herr | |
| 2016/0074182 | A1 | 3/2016 | Celebi | |
| 2016/0095720 | A1 | 4/2016 | Behzadi | |
| 2016/0113831 | A1 | 4/2016 | Hollander | |

OTHER PUBLICATIONS

T. Ménard, G. Grioli and A. Bicchi, "A real time robust observer for an Agonist-Antagonist Variable Stiffness Actuator", Robotics and Automation (ICRA), 2013 IEEE International Conference (Karlsruhe, May 6-10, 2013).
Giorgio Carpino, Dino Accoto, Fabrizio Sergi, Nevio Luigi Tagliamonte and Eugenio Guglielmelli, "A Novel Compact Torsional Spring for Series Elastic Actuators for Assistive Wearable Robots", J. Mech. Des 134(12), 121002 (Oct. 19, 2012).
Matteo Laffranchi, Hide Sumioka, Alexander Sproewitz, Dongming Gan, Nikos G. Tsagarakis, "Compliant Actuators, Adaptive Modular Architectures for Rich Motor Skills (AMARSi)", ICT-248311 D2.1 (Mar. 2011).
Gill A. Pratt and Matthew M. Williamson, "Series Elastic Actuators", IEEE, 399-406 (1995).
Matthew M. Williamson, "Series Elastic Actuators", Masters Thesis, Department of Electrical Engineering and Computer Science, Massachusetts Institute of Technology (Feb. 1995).
Micromotion, Product Catalog, "Precision Microactuators", downloaded Jan. 16, 2015 from http://www.orlin.co.uk/PDFs/Micromotion_product_brochure.pdf.
Schaeffler KG, Linear technology Division, "Miniature Linear Actuator with Toothed Belt Drive", Series MLFI20-ZR (Jan. 2006).
Nicholas Paine, "Design and Control Considerations for High-Performance Series Elastic Actuators", IEEE/ASME Transactions on Mechatronics, 1-11 (2013).
D.F.B. Haeufle, M.D. Taylor, S. Schmitt, H. Geyer, "A clutched parallel elastic actuator concept:towards energy efficient powered legs in prosthetics and robotics", 2012 4th IEEE RAS & EMBS International Conference on Biomedical Robotics and Biomechatronics (BioRob) (Rome, Jun. 24-27, 2012).
Markus Baeuml, Florian Dobre, Harald Hochmuth, Manfred Kraus, Hartmut Krehmer, Roland Langer, Dominik Reif, "The Chassis of the Future", The Schaeffler Symposium Book (Schaeffler Technologies AG & Co. KG, 2014).
Fabrizio Sergi, Melissa M. Lee, and Marcia K. O'Malley, "Design of a series elastic actuator for a compliant parallel wrist rehabilitation robot", 2013 IEEE International Conference on Rehabilitation Robotics , pp. 1-6 (Seattle, WA, Jun. 24-26, 2013).
Sidharth Iyer, "Modeling and Testing of a Series Elastic Actuator with Controllable Damping", Master's Thesis, Worcester Polytechnic Institute (Jan. 2012).
Agostino De Santis, Bruno Siciliano, Alessandro De Luca, Antonio Bicchi, "An atlas of physical human-robot interaction", Mech. Mach. Theory (2007).
Michael David Taylor, "A Compact Series Elastic Actuator for Bipedal Robots with Human-Like Dynamic Performance", Master's Thesis, Robotics Institute, Carnegie Mellon University (Aug. 2011).

* cited by examiner

SPRING AUGMENTED ORTHOTIC OR PROSTHETIC EQUIPPED WITH A COMPACT PARALLEL ECCENTRIC ACTUATOR

CROSS-REFERENCE TO RELATED APPLICATION

This application is a continuation-in-part application of U.S. patent application Ser. No. 14/869,994, filed Sep. 29, 2015, having the same inventor and entitled "COMPACT PARALLEL ECCENTRIC ROTARY ACTUATOR," which is incorporated herein by reference in its entirety. This application also claims the benefit of priority from U.S. provisional application No. 62/107,734, filed Jan. 26, 2015, having the same inventor and entitled "SPRING AUGMENTED ORTHOTIC COMPACT PARALLEL ECCENTRIC ACTUATOR," and which is incorporated herein by reference in its entirety. This application also claims the benefit of priority from U.S. provisional application No. 62/057,216, filed Sep. 29, 2014, having the same inventor, entitled "COMPACT PARALLEL ECCENTRIC ROTARY ACTUATOR," and which is incorporated herein by reference in its entirety, and also claims the benefit of priority from U.S. Provisional Application No. 62/210,223, filed Aug. 26, 2015, having the same inventor and entitled "COMPACT PARALLEL ECCENTRIC ROTARY ACTUATOR," which is incorporated herein by reference in its entirety.

FIELD OF THE DISCLOSURE

The present disclosure relates generally to orthotics and prosthetics, and more particularly to spring activated orthotics/prosthetics equipped with a parallel eccentric actuator.

BACKGROUND OF THE DISCLOSURE

At present, nearly 1 in 5 people in the U.S. are disabled. Many of these people rely on mechanical assistance to function in everyday life. Thus, for example, approximately 10 million people in the U.S. alone would benefit from cost-effective and compact orthotic exoskeleton support. Such support would enable these people to participate in Activities of Daily Living (ADL), including productive work to provide self-sufficiency.

SUMMARY OF THE DISCLOSURE

Figure 1:
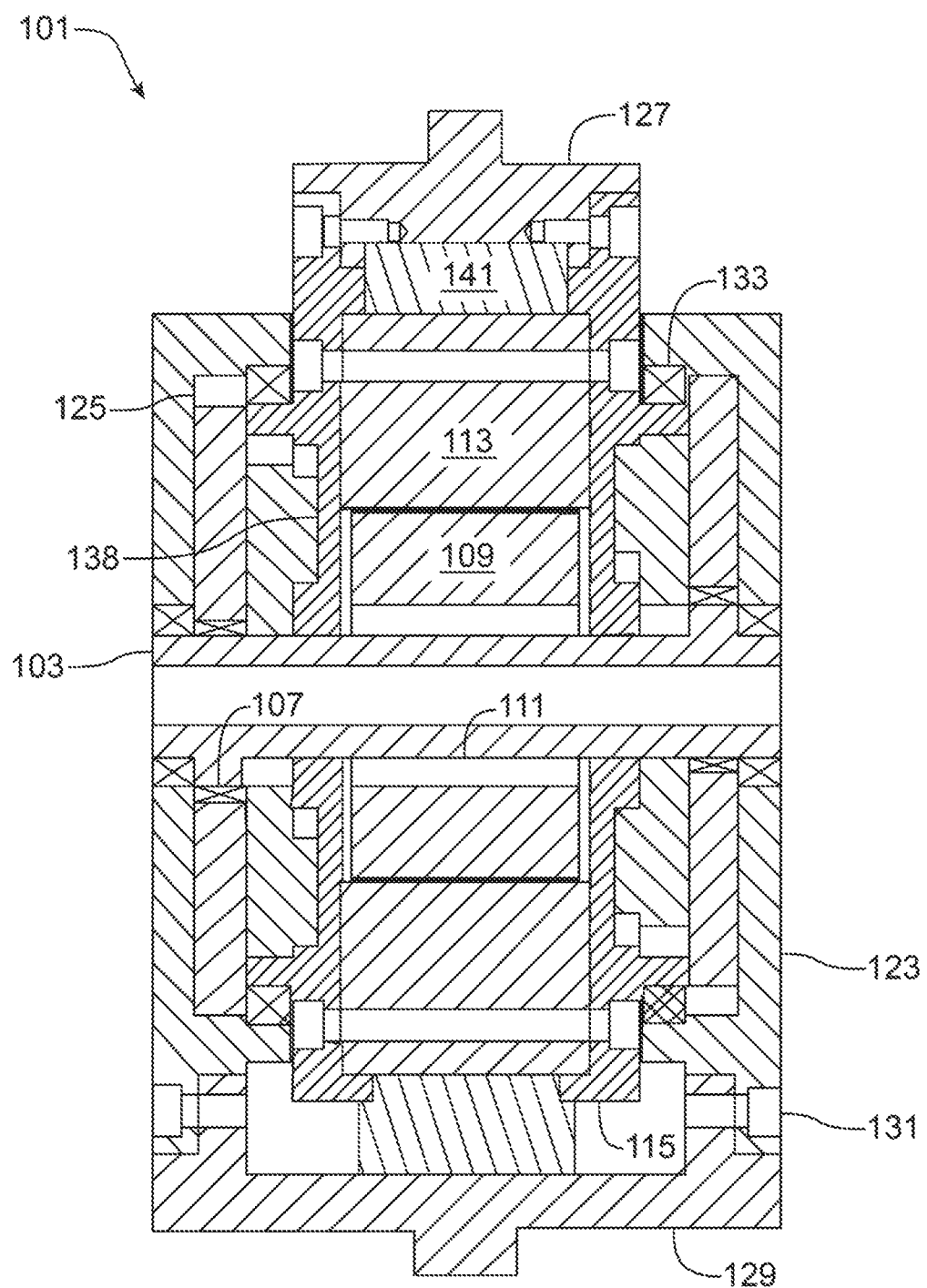
FIG. 1 is an illustration of a particular, non-limiting embodiment of an orthotic/prosthetic actuator in accordance with the teachings herein which is based on a compact parallel eccentric.

In one aspect, an orthotic actuator is provided which comprises (a) a parallel eccentric gear train which terminates on a first end in a first plate, and which terminates on a second end in a second, rotatable plate, and (b) a spring which is disposed between these adjacent plates. The actuator preferably utilizes Oldham coupling, by way of a pair of crosslinks disposed on each side of the motor, to restrain rotation of the dual parallel eccentric gears in the actuator, while permitting their linear oscillation. The crosslinks are preferably equipped with a tongue/spline lubrication system to provide continuous lubrication to the mated and loaded crosslink tongue and groove surfaces.

DETAILED DESCRIPTION

In recent years, many advances have been made in the fields of orthotics and prosthetics. Consequently, many disabled persons are now able to function with greater self-sufficiency, thus allowing them to participate more fully in ADL. Despite these advances, however, the mechanics of the human anatomy has proven difficult to replicate. Thus, further improvements in orthotic and prosthetic devices are still required to allow these devices to more closely replicate the human kinematics they are designed to mimic.

Mechanical actuators are key components of many orthotic and prosthetic devices. However, some of the more demanding orthotic and prosthetic applications (such as, for example, those involving knee, hip and ankle joints) require compact actuators with maximum torque density and maximum efficiency. Actuators in these applications are typically required to provide continuous torque of at least 100 ft-lb., and peak torque of at least 200 ft-lb. These requirements exceed the performance metrics that many current actuators are capable of providing, especially in a compact form factor.

Spring energy storage has been utilized in the art to augment active actuation modules. In particular, spring energy storage has been utilized to reduce energy consumption and create larger return forces, as might be needed in activities such as stair climbing. Spring energy storage may be implemented either in series (the SEA) or in parallel (the PEA), thus posing the question as to which of these options is best suited for various orthotic joint actuations.

Passive energy storage springs are frequently utilized to replace some of the function of the foot or ankle for lower limb amputees. This approach is especially useful for light duty running and walking. In heavy duty climbing (such as that involved in climbing a set of stairs), the spring is typically embedded in a structure that operates in parallel to the foot/ankle combination, and mechanically duplicates the kinematics of this portion of the anatomy.

In a normal human body, the toes act in series with the foot/ankle kinematics to provide a softening "touch" that reduces shock in the stepping cycle. Some attempts have been made in the art to duplicate this effect in orthotic and prosthetic devices.

One such approach, which has been replicated by many others, is described in Gill Pratt & Matthew Williamson, "Series Elastic Actuators", IEEE 399-406 (1995). This approach involves placing a passive spring "in front" of the foot/ankle structure. In some implementations of this approach, the foot/ankle structure may additionally be supported by a passive spring which is arranged in-parallel. In other implementations, the foot/ankle structure may additionally be supported by a spring which is arranged in parallel with an active orthotic actuator at the ankle location. Both of the foregoing approaches may have merit.

Although the human toes serve a shock buffer/spring energy function, they only do so in a subsidiary role, leaving the ankle to do most of the real "work" (motion and force control). It is thus desirable to create an active actuator to replicate the function of the human ankle. This application requires the actuator to be unusually light (torque dense) with a high sensitivity to body movement and patient command (this latter consideration is a major issue for the technology). Given a fully developed orthotic actuator, it thus becomes desirable to minimize the size and weight of the actuator and to maximize its energy efficiency.

It has now been found that the foregoing goals may be met by using a Parallel Elastic Actuator (PEA) arrangement (that is, a spring in parallel with the actuator, rather than in series with it as in the SEA). It has further been found that this PEA is ideally suited for demanding operations, such as climbing a set of stairs.

As previously noted, it is typically preferred that orthotic or prosthetic actuators are extremely light and compact. The preferred embodiment of the PEA arrangements disclosed herein uses a Compact Parallel Eccentric (CPE) actuator. Such an actuator is capable of producing 100 ft-lb. continuous torque in a 2.5" wide and 3.5" diameter package, weighing about 3.5 lb., and may produce a peak torque of up to 200 ft.-lb. for short periods. This system responds to either client voice commands (such as, for example, be stiff, climb, be efficient, be smooth, be quiet) or to body sensor signals which cyclically monitor/energize the stator coils with needed voltage and current levels. Consequently, the PEA is active or responsive to human command. The spring in the PEA may be engaged at any time in the cycle and may be preloaded to any designed torque level to support or augment the torque demands on the actuator in the PEA.

It should be noted that, in comparison to the PEA, the SEA has no similar flexibility. The SEA is only a buffer to shock and provides a limited capacity for energy storage in a small part of the motion cycle. Further, once its parameters are set for a given cycle (spring constant and preload), it cannot be changed by the client.

The PEA, by contrast, permits a complete set of spring constants, preloads, action points in the cycle, on/off, and other such parameters. The PEA approach described may also be utilized in hip and knee applications, especially in cyclic operations of walking and climbing stairs. These functionalities may be disengaged by a "relax" command from the client (i.e., when relaxing in a chair). Lighter PEAs under special control commands may be made to work in an orthotic or prosthetic arm.

In orthotic applications, voice commands and body sensor signals may be combined to control the PEAs. These orthotic arm PEAs will typically be required to be much smaller and more efficient, and may be driven with piezoelectric prime movers. Preferably, voice commands may be utilized as the primary input signals for prosthetic arms, as in programming robot manipulators. These commands may be standardized for operation on call with speed, load values, stiffness values, and other suitable parameters set by voice command.

The devices and systems disclosed herein are preferably based on compact parallel eccentric actuators with minimal rolling element bearings. These actuators are preferably supported by a solenoid actuated dog clutch and a large diameter spiral spring using rectangular cross-section coils. Such actuators may provide performance metrics—such as torque and volume density, efficiency, stiffness, responsiveness, and durability—which exceed those of prior art actuators by orders of magnitude. Actuators of this type may advantageously be provided with standardized quick-change interfaces, thus yielding actuator modules which may be rapidly replaced (in plug-and-play fashion) by the client or the caregiver. This approach removes one of the serious issues on availability (rapid repair in place) of the orthotic system in the home or in the workplace.

Figure 3:
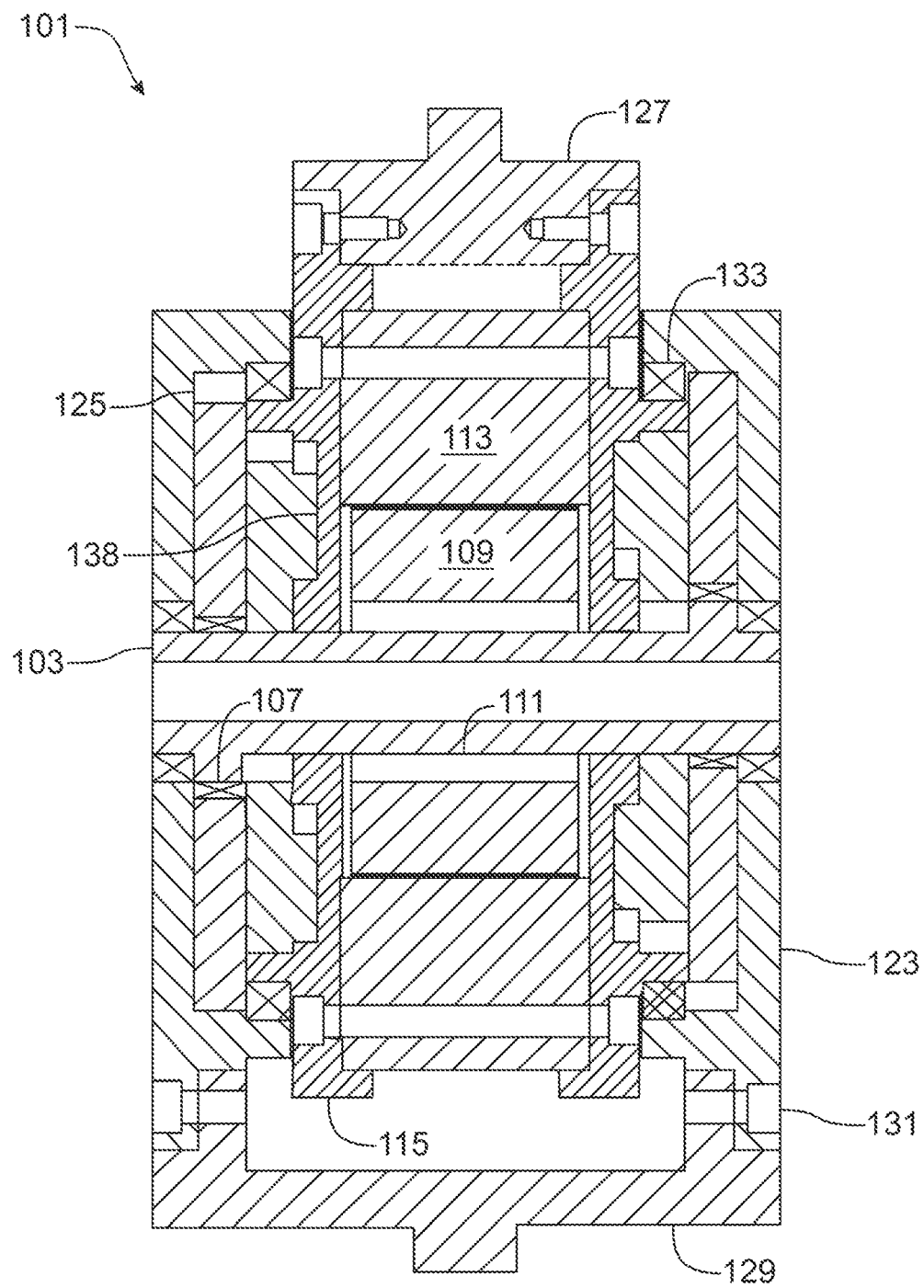
FIG. 3 is an illustration of a compact parallel eccentric actuator assembly.

FIG. 1 depicts a particular, non-limiting embodiment of a compact parallel eccentric orthotic actuator in accordance with the teachings herein. The compact parallel eccentric actuator on which the device of FIG. 1 is based is depicted in FIG. 3.

The particular CPE rotary actuator 101 depicted in FIG. 1 comprises a crankshaft 103 equipped with first and second eccentrics 107. A rotor 109 is rotatably mounted on the crankshaft 103 and is separated therefrom by way of a rotor spacer 111. A stator 113 is rigidly supported on a pair of internal stator support plates 115 in closely spaced-apart relation to the rotor 109.

The CPE rotary actuator 101 is further equipped with first and second crosslinks 117 and with first and second eccentric gears 121. Each eccentric gear 121 is disposed between a crosslink 117 and one of first and second output plates 123 (also referred to herein as output gears)

As seen in FIG. 1, each crosslink 117 has a gap 125 adjacent thereto, and engages adjacent surfaces of the corresponding eccentric gear 121 and the internal stator support plate 115 across a tongue and groove surface 119. The CPE rotary actuator 101 is further equipped with a reference link 127, an output link 129, attachment lugs 131, principal bearings 133, shaft bearings 135, an internal gear 137, a rotor spacer 139, and an orthotic spring 141.

The CPE rotary actuator 101 of FIG. 1 leverages the structural integrity of the (preferably circular) stator 113 of the prime mover to effectively resist forces/moments in all directions. In particular, the rigidity of the stator 113 is enhanced by the addition of the two internal stator support plates 115, which are bolted to the sides of the stator 113 with small attachment wedges 145 to create a solid mating structure. Further details of CPE rotary actuators of the type depicted in FIG. 1 may be found in commonly assigned U.S. Ser. No. 14/869,994 (Tesar), entitled "COMPACT PARALLEL ECCENTRIC ROTARY ACTUATOR", and filed on Sep. 29, 2015, which is incorporated herein by reference in its entirety.

In the actuator modules disclosed herein which are based on Compact Parallel Eccentric (CPE) actuators of the type depicted in FIG. 1, the motor is used as the structural backbone of the device. This arrangement provides for substantial weight reduction. The rotor drives a crankshaft which is very lightly loaded to enable small supporting bearings. The crankshaft contains two eccentrics to drive two parallel eccentric gears (one on each side) which oscillate without rotation constrained by two tongue and grooved cross-links. These parallel gears preferably use circular arc gear teeth to drive internal gears as part of the structure of the output plates. These output plates then attach to the orthotic links of the exoskeleton.

One significant advantage of the foregoing actuator is its simplicity. In a preferred embodiment, the actuator utilizes only two widely-spaced, large diameter, small cross-section bearings (at low oscillating speeds) to directly carry the out-of-plane joint load. The crankshaft bearings are primarily utilized for centering purposes, since they are lightly loaded, and no other rolling element bearings are employed. Moreover, the large diameter parallel gears are virtually noiseless because of the simple meshing of up to 5 teeth in the circular arc tooth meshes. By contrast, prior art gearing typically requires high speed, heavily loaded bearings that take up space and generate noise.

In the preferred embodiment, the actuators disclosed herein are further advantageous because of their thinness. Very thin gears can carry a very high load, with no backlash or meshing noise. Hence, in addition to being technically superior as compared to prior art actuators, the preferred actuators are virtually noiseless, which is a prime consideration in orthotic and prosthetic applications.

The systems, devices and methodologies disclosed herein preferably utilize voice commands to allow the wearer of the orthotic system to command the actuator to perform a needed function. Some particular, non-limiting examples of such commands and functions are set forth in TABLE 1 below.

TABLE 1

Voice Command Examples

| Command | Function |
| --- | --- |
| Stand | To raise oneself when getting out of bed or off a chair. This may require a peak torque at each knee of 200 ft-lb. |
| Walk | Use the actuator to drive the ankle, knee, and hip joints in unison to repeat a trained walking cycle at maximum efficiency. |
| Climb Stairs | Coordinate all leg actuators to enable a sequence of stair steps. This embedded sequence would be established during wearer training and may require 100 (+) ft-lb. peak torques. |
| Exercise | Either walking at various speeds on a treadmill or an exercise bike based on repetitive embedded data from client training. |
| Relax | Exoskeleton is trained to take body-generated signals (force sensing) from the client legs/arms to command the actuators to move the exoskeleton with no active force participation by the wearer. |

It will be appreciated from TABLE 1 that a variety of command options are possible with the orthotic systems disclosed herein. Hence, the embedded/structured plans (intelligence) may be an important aspect of these systems.

The cyclic energy balance is another important aspect of the preferred embodiment of the orthotic and prosthetic actuators disclosed herein. Springs are an effective device to store and return energy in repeating exoskeleton cycles, and may be used to reduce energy demands on the portable orthotic power supply (especially useful in some ADL functions). Springs may also provide torque output to reduce peak torque demands on the actuator, perhaps by up to 50%. This may enable actuator weight reductions of 40% or more. For example, it now appears feasible to create a peak torque actuator with spring of 200 ft-lb. at 5 lb. weight, thus yielding an orthotic or prosthetic actuator assembly which is unusually efficient, virtually noiseless, and which fits under normal external garments.

Figure 2:
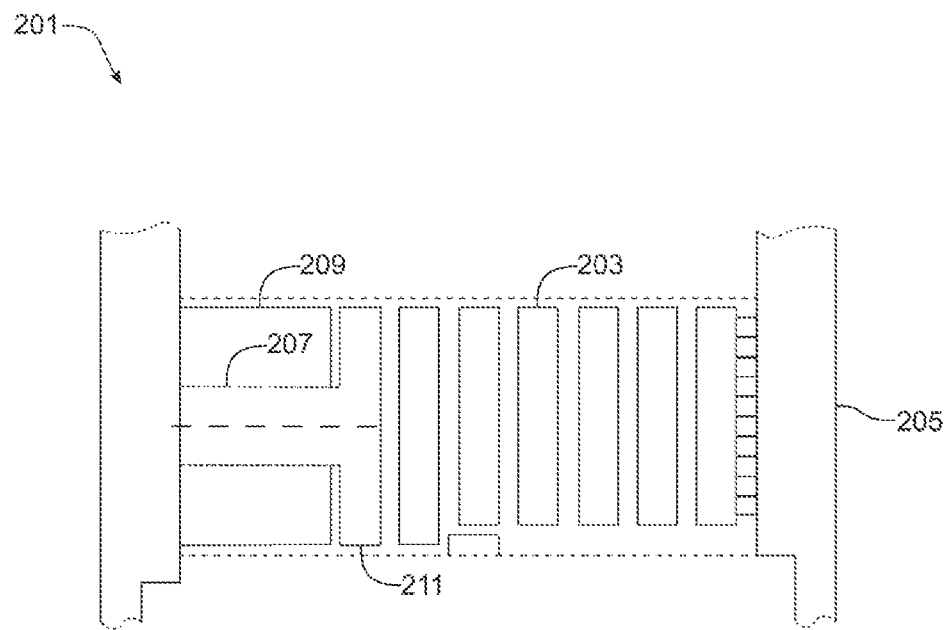
FIG. 2 is an illustration of a clutched spring for an orthotic actuator.

As seen in FIG. 2, the orthotic and prosthetic devices and systems disclosed herein preferably utilize a solenoid 209 commanded by a dog clutch 211 to drive a spiral spring coil 203. The spiral spring coil 203 and the dog clutch 211 are disposed between first and second opposing stator plates 212. Spiral spring coils of rectangular cross-section are capable of 100 ft-lb. torque in a small package in a rotation of 90°. In a preferred embodiment, the spiral spring coil 203 is approximately 4" in diameter with four $\frac{1}{8}$"×$\frac{1}{2}$" coils using spring steel in a total volume of 3 in.$^3$ and a weight of 0.9 lb. The required large diameter solenoid 209 and dog clutch 211 is expected to weigh 0.6 lb. to create a subassembly of 1.5 lb. The dog clutch 211 will use face teeth very similar to those found in synchro clutches in auto transmissions. Soft surface materials may be utilized to reduce their closing noise. Each position of the dog clutch face attached to the spiral spring coil 203 will preferably be held with several detents 214 (perhaps 4) on its periphery to enable the solenoid 209 to be energized only when coupling/uncoupling the spring coil 203. Hence, the spring coil 203 is only engaged when it is needed for cyclic energy balance, and would be inactive when the joint is carrying very little torque.

The advantage of this spring assembly is evident from an energy balance/peak torque demand functional requirement, and it may be fitted within the existing CPE actuator geometry with virtually no packaging demands. In addition to offering various other possible advantages (such as, for example, being compact, efficient and noiseless), the resulting actuator is also elegant in its geometry and response to wearer commands, and allows for the expansion of orthotic technology to a wide range of exoskeleton requirements.

The CPE was designed specifically to be exceptionally rugged and to remove all critical rolling element bearings, primarily because such bearings reduce torque density (increase volume demands) and reduce stiffness and shock resistance (due to their point or line contacts). This was achieved by using the Oldham coupling concept to restrain the rotation of the dual parallel eccentric gears while permitting their linear oscillation. As seen in FIG. 3, this restraint is provided by a pair of cross links 117 on each side of the internal strong back motor. These cross links 117 use multiple tongues to mate with grooves in the stator plate 138 and the oscillating parallel eccentric gears 121. These mating tongues and grooves primarily carry the torque loads in the CPE.

These mating surfaces oscillate (to and fro) for each rotation of the crankshaft 103 whose eccentrics 107 drive the parallel eccentric gears 121. The range of the sliding motion is somewhat more than the height of the teeth in the eccentric gears 121. Hence, the relative motion is small, while the surface pressure depends on the geometry and effective length of all the mated tongue and groove combinations. Hence, it is essential that these mated and loaded surfaces be well lubricated.

Figure 4:
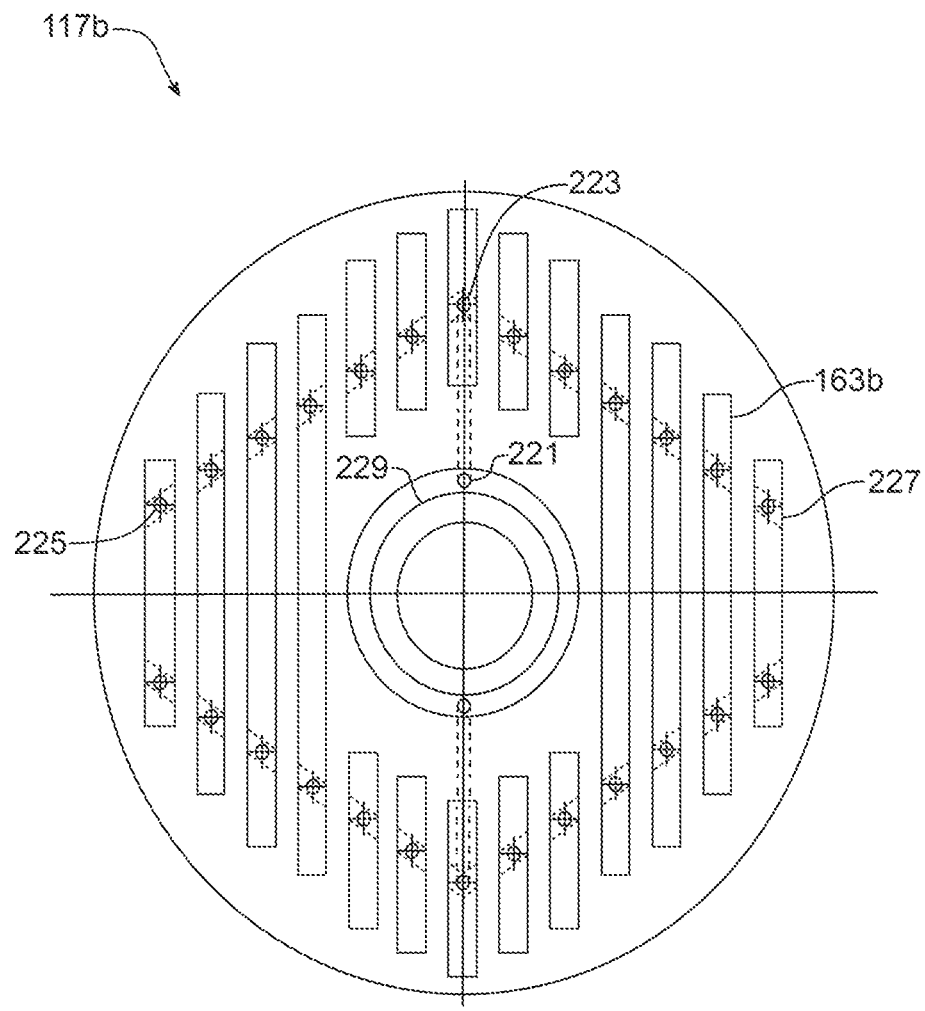
FIG. 4 is a front view, partially in section taken along a plane perpendicular to the longitudinal axis of the crankshaft, of a maximum load/stiffness capacity crosslink suitable for use in the oscillating cross link of FIGS. 1 and 3. This particular embodiment depicts a generalized concept of tongue and grooves with 2 oil pumps providing pressurized oil to a continuous cross channel machined in the base of the tongues on the cross link and the top of the grooved face link mating surface.
Figure 5:
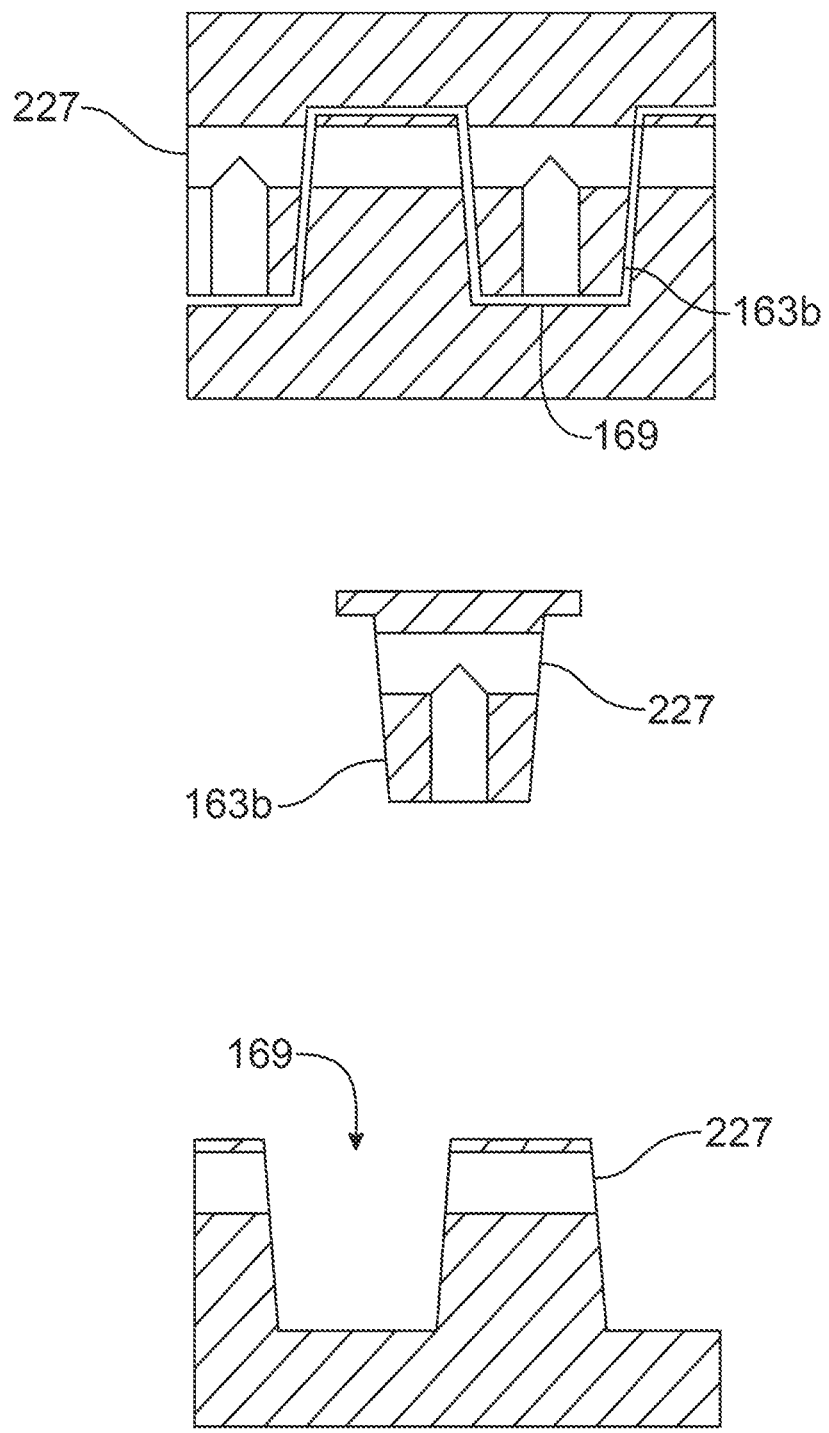
FIG. 5 is a series of cross-sectional views illustrating the tongue and groove configuration of the crosslink of FIG. 3.

FIGS. 4-5 illustrate a particular, non-limiting embodiment of a lubrication system which may be utilized in the orthotic systems and devices disclosed herein. Thus, FIG. 4 is a front view, partially in section taken along a plane perpendicular to the longitudinal axis of the crankshaft, of a maximum load/stiffness capacity crosslink 117b suitable for use in the oscillating cross link of the actuators of FIGS. 1 and 3. This particular embodiment depicts a generalized concept of tongue and grooves with two oil pumps 221 providing pressurized oil to a continuous cross channel machined in the base of the tongues 163b on the crosslink 117b and the top of the grooved face link mating surface. The crosslink 117b further includes first and second supply ports 223, a groove supply port 225, a tongue channel 227, and a crankshaft collar 229. The tongue and groove configuration of the crosslink of FIG. 4 is depicted in the series of cross-sectional views of FIG. 5.

It is to be understood that the lubrication system of FIGS. 4-5 is not limited in use to orthotics systems and devices, but is more broadly applicable to a wide range applications for CPE actuators. Thus, for example, the lubrication system depicted in FIGS. 4-5 may find end uses in CPE applications ranging from those with demanding duty cycles (such as, for example, construction and earth moving equipment) to low cost applications with modest duty cycles (such as, for example, orthotic joint drivers). For this reason, both high and low duty cycle applications are described herein.

High duty cycle applications typically require high RPMs (to reduce motor size and improve torque density) and high load levels (with substantial shock in some cases). This implies high power and high demands on the mating tongue and groove surfaces. To reduce friction and wear, these surfaces typically must be lubricated. In this application spectrum, a passive valved pump is preferably utilized in the cross links using the existing oscillation that generates a pulse of pressure in the available lubricant. This pump, then, sends pressurized lubricant through a labyrinth of channels to supply continuous oil to the mating tongue and groove surfaces.

In low duty cycle applications, the goal is to dramatically reduce costs while still providing high torque density and reasonable durability. For such applications, it is preferred to periodically inject grease in a special pressurized spring-loaded container inside the crankshaft inner channel. This injection may be manual (e.g., with the use of a grease Zerk gun) on a timed basis to maintain supply to the pumping gap available in each cross link. The grease used for this purpose is preferably low viscosity grease with good adhesion properties. If a grease gun is utilized to apply the grease, the grease gun pressurizes the spring-loaded container, which then supplies the grease to the cross link gaps. The cross link gaps, in turn, then drive the grease through the channels to the mating tongue and grooves. This supply of grease may also lubricate the crankshaft bearings, the large diameter principal bearings, and the gear tooth meshes on the parallel gears.

The lubrication systems described herein provide a very cost-effective and customer-managed lubrication system. The potential application may require an output oscillation of 1 cycle per sec. With a 100-to-1 reduction ratio, this means that the crankshaft would rotate at 6000 RPM, as would the oscillation in the tongue and grooves. This simple and somewhat uncertain lubrication method would, then, demand a lower effective load on the mating surfaces, which is typically necessary to keep cost down. Further, this peak RPM/load combination would be unusual, as in orthotics, where it might occur for a few minutes once or twice each day. It now appears that this is entirely feasible to enable a very broad range of low duty cycle applications.

The above description of the present invention is illustrative, and is not intended to be limiting. It will thus be appreciated that various additions, substitutions and modifications may be made to the above described embodiments without departing from the scope of the present invention. Accordingly, the scope of the present invention should be construed in reference to the appended claims. It will also be appreciated that the various features set forth in the claims may be presented in various combinations and sub-combinations in future claims without departing from the scope of the invention. In particular, the present disclosure expressly contemplates any such combination or sub-combination that is not known to the prior art, as if such combinations or sub-combinations were expressly written out.

What is claimed is:

1. An actuator for orthotics or prosthetics, comprising:
   a parallel eccentric gear train which terminates on a first end in a first plate, and which terminates on a second end in a second, rotatable plate which is adjacent to said first plate; and
   a spring disposed between the first and second plates; wherein said spring is driven by a solenoid commanded dog clutch.

2. The actuator of claim 1, wherein said parallel eccentric gear train includes an Oldham coupling.

3. The actuator of claim 2, further comprising first and second parallel eccentric gears, wherein said Oldham coupling restrains the rotation of said first and second parallel eccentric gears.

4. The actuator of claim 3, wherein said Oldham coupling permits the linear oscillation of said first and second parallel eccentric gears.

5. The actuator of claim 3, wherein said Oldham coupling includes first and second crosslinks.

6. The actuator of claim 1, wherein said actuator is equipped with first and second eccentrics that are driven 180° out of phase, wherein said first eccentric drives a first parallel gear and the second eccentric drives a second parallel gear.

7. The actuator of claim 6, wherein said first eccentric is equipped with a first crosslink, and wherein said second eccentric is equipped with a second crosslink.

8. The actuator of claim 7, wherein said first eccentric comprises a first parallel eccentric gear, and wherein said first crosslink is equipped with a first plurality of tongues which mate with a first set of grooves in said first stator, and which mate with a second set of grooves in said parallel eccentric gear.

9. The orthotic actuator of claim 8, further comprising a second pair of crosslinks.

10. The actuator of claim 9, wherein said second eccentric comprises a second parallel eccentric gear, and wherein said second crosslink is equipped with a second plurality of tongues which mate with a third set of grooves in said stator, and which mate with a fourth set of grooves in said second parallel eccentric gear.

11. The actuator of claim 1, wherein said spring is a spiral spring.

12. The actuator of claim 1, wherein said dog clutch is attached to said spring.

13. The actuator of claim 12, wherein said dog clutch is equipped with a clutch face having a plurality of face teeth thereon.

14. The actuator of claim 13, further comprising a plurality of détentes which maintain each position of the dog clutch face.

15. The actuator of claim 1, wherein said spring is preloaded to a predetermined torque level.

16. The actuator of claim 1, wherein said actuator controls the motion of an exoskeleton, and wherein said spring is adapted to store and return energy in repeating cycles of said exoskeleton.

* * * * *